United States Patent [19]

Piez et al.

[11] Patent Number: 4,795,467
[45] Date of Patent: Jan. 3, 1989

[54] XENOGENEIC COLLAGEN/MINERAL PREPARATIONS IN BONE REPAIR

[75] Inventors: Karl A. Piez, Menlo Park; Bruce B. Pharriss, Palo Alto; George H. Chu, Sunnyvale; Thomas L. Smestad; Diana Hendricks, Palo Alto, all of Calif.

[73] Assignee: Collagen Corporation, Palo Alti, Calif.

[21] Appl. No.: 848,443

[22] Filed: Apr. 4, 1986

Related U.S. Application Data

[63] Continuation-in-part of Ser. No. 717,072, Mar. 28, 1985, abandoned.

[51] Int. Cl.$^4$ ............................................. A61F 2/28
[52] U.S. Cl. ........................ 623/16; 128/92 YG; 128/92 YR; 128/92 YQ; 514/801
[58] Field of Search ............... 128/92 C, 92 CA, 92 R, 128/92 YO, 92 YOR, 92 YOG, 92 YG, 92 XP, 92 YQ, 92 W, DIG. 8, 92 Y, 92 N, 92 YR; 623/11, 16 B, 16 D, 16 E, 16 F, 66, DIG. 1; 106/161; 424/773, 801; 427/2

[56] References Cited

U.S. PATENT DOCUMENTS

| | | | |
|---|---|---|---|
| 3,443,261 | 5/1969 | Battista et al. | 3/1 |
| 3,767,437 | 10/1973 | Cruz, Jr. | 106/161 |
| 4,192,021 | 3/1980 | Deibig et al. | 623/16 |
| 4,314,380 | 2/1982 | Miyata et al. | |
| 4,349,470 | 9/1982 | Battista | 260/117 |
| 4,472,840 | 9/1984 | Jefferies | 623/16 |
| 4,516,276 | 5/1986 | Mittelmeier et al. | 3/1.91 |
| 4,563,350 | 1/1986 | Nanthan et al. | 424/95 |
| 4,582,640 | 4/1986 | Smestad et al. | 128/DIG. 8 X |
| 4,596,574 | 6/1986 | Vrist | 623/16 |
| 4,622,553 | 11/1986 | Ries et al. | 427/2 |

FOREIGN PATENT DOCUMENTS

| | | |
|---|---|---|
| 0030583 | 6/1981 | European Pat. Off. |
| 0052288 | 5/1982 | European Pat. Off. ...... 128/DIG. 8 |
| 5858041 | 4/1983 | Japan . |

OTHER PUBLICATIONS

Lemons, J. et al., Second World Congress of Biomaterials in Washington, D.C., (1984), 13–16.
Gross, B. D. et al., Oral Surg (1980), 49:21–26.
Hayashi, K. et al, Orthop Traumat Surg (1982), 99: 265–269.
Levy, P. et al, J. Periodontal (1981), 52: 303–306.

Primary Examiner—Richard J. Apley
Assistant Examiner—Paul B. Prebilic
Attorney, Agent, or Firm—Ciotti & Murashige, Irell & Manella

[57] ABSTRACT

A composition for use in bone repair, in particular, in onlay procedures, which comprises calcium phosphate mineral particles in admixture with atelopeptide reconstituted fibrillar collagen preparations is disclosed. This composition is non-immunogenic and encourages the fusion of host bone with new bone growth through the implant. Additional processes for curing the implant to improve its compressive strength include heat curing, maturation, and cross-linking.

27 Claims, 1 Drawing Sheet

XENOGENEIC COLLAGEN/MINERAL PREPARATIONS IN BONE REPAIR

This application is a continuation-in-part of U.S. Ser. No. 717,072, filed Mar. 28, 1985, now abandoned.

TECHNICAL FIELD

This invention relates to the field of hard tissue repair. Specifically, it relates to the use of mixtures of atelopeptide reconstituted fibrillar collagen with hydroxyapatite or calcium phosphate mineral preparations in bone grafts.

BACKGROUND ART

The general notion of using mixtures or combinations of collagen protein and bone minerals in effecting hard tissue repair has been known for some time. As bone itself is comprised of these minerals, along with collagen, it seemed promising to utilize this combination. However, implementation of this concept has not proved to be as simple as might have been supposed. First, it has been difficult to obtain a preparation which has the correct physical properties to provide a support matrix for bone in-growth so as to result in a successful repair. Second, unless the proteinaceous component was derived from tissue of the same individual who is the recipient of the implant, inflammatory responses are commonplace as a result of the immunogenic character of the implant. This problem is not entirely obviated by using collagen derived from the same species, but performance is improved over that resulting from use of collagen from, for example, bovine or porcine sources in humans. Thus, the form of the collagen used is critical to the success of the implant. The form of the mineral component is not critical, except the resulting mixtures must have handling properties suitable for the indications.

Reports of attempts to use the collagen/mineral combination are numerous. For example, Lemons, J., et al., reported at the Second World Congress of Biomaterials in Washington, D.C., Apr. 27-May 1, 1984, on attempts to utilize collagen along with commercial hydroxyapatite and calcium phosphate to repair artificially created lesions in rabbits. The use of these mixtures did not result in reunion of the lesions. A control experiment using fresh autogenous bone, however, was successful in producing a union. Similarly, Levy, P., et al, *J Periodontal* (1981), 52: 303-306, were unsuccessful in their attempts to utilize collagen/mineral gel implants to repair intra-bony defects in root canals of canine or monkey teeth. Gross, B. C., et al., *Oral Surg* (1980), 49:21-26, reported limited success in using mixtures of reconstituted lyophilized calfskin collagen in admixture with a hydroxyapatite preparation to induce bone growth through subperiosteal implants in monkeys. Various others have reported use of forms of collagen which clearly contain telopeptides, a major source of immunogenicity of collagen, in combination with minerals in bone repair. See, for example, Hayashi, K. et al., *Arch Orthop Traumat Burg* (1982) 99:265-269; Battista, U.S. Pat. No. 4,349,490 (using a hydrated gelatin); Cruz, Jr., U.S. Pat. No. 3,767,437 (using a calcium-precipitated form of collagen); and Battista, et al., U.S. Pat. No. 3,443,261 (utilizing, in addition to calcium phosphate, a "new form" of collagen which contains microcrystals of aggregated tropocollagen units.

Miyata, et al., U.S. Pat. No. 4,314,380, utilized a mineral backbone prepared directly by treatment of animal bone to remove all organic materials, which was then coated with an atelopeptide collagen. Japanese Application No. J58/058041, published Apr. 6, 1983, discloses a spongy porous calcium phosphate material having pores treated with atelopeptide collagen. The collagen derives from collagen-in-solution having a concentration of not more than 2% by weight. The Japanese application reports the advance of osteoblasts into the pores of the material and new bone growth. European patent Application, publication No. 030583, published June 24, 1981, discloses use of COLLAGENFLEECE® in admixture with hydroxyapatite in bone repair. This collagen material is a commercial product, is obtained from animal hide by proteolytic digestion, and is lyophilized and sterilized by gamma irradiation. This collagen preparation forms a soft membrane-like material but does contain telopeptides and is partially degraded by the processing.

In summary, there have been numerous attempts to use combinations of calcium phosphate mineral components and collagen in various forms of bone defect repair with mixed success. It is clear that the art contains no perfect composition which can be relied upon to provide satisfactory results in a predictable manner in connection with a specific process. A reproducibly effective preparation for encouraging bone in-growth was, until the present invention, lacking in the art,

DISCLOSURE OF THE INVENTION

The present invention provides a composition containing a collagen and a calcium phosphate mineral component which provides a successful support for in-growth of new bone tissue. The mineral component can be one of a variety of bone-compatible calcium phosphate salts such as hydroxyapatite (HA) or tricalcium phosphate: the collagen is a specific form: reconstituted fibrillar atelopeptide collagen. The mixture can be supplied in either wet or dry form, and can be, if desired, cross-linked to a predetermined extent. The physical and handling properties of the mixtures can be improved by a number of curing processes, including heat, maturation of the wet mixture and specific cross-linking. The composition is effectively used in grafting procedures both in connection with skeletal bone and in periodontal procedures.

In other aspects, the invention is directed to methods of bone augmentation or repair using the compositions of the invention and to a method of coating the pores of a calcium phosphate mineral porous block with collagen.

MODES OF CARRYING OUT THE INVENTION

Figure 1:
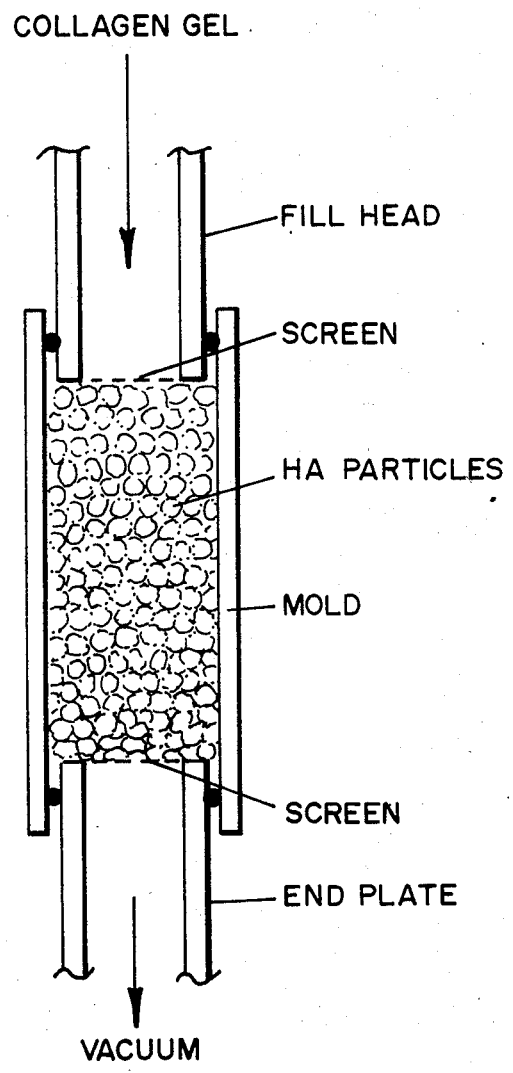
FIG. 1 shows a method to prepare a collagen-coated mineral support block.

The compositions of the invention can use a variety of calcium phosphate mineral component materials. As used herein, "calcium phosphate mineral" materials refers to those materials composed of $Ca^{+2}$ and phosphate ions, regardless of the microstructure protonation status of the phosphate, or extent of hydration. Calcium phosphate mineral materials include a variety of forms, such as the commercially available forms of tricalcium phosphate for example. SYNTHOGRAFT® tricalcium phosphate, or of hydroxyapatite such as PERIO- GRAF®, ALVEOGRAF®, INTERDORE®, ORTHOMATRIX™ HA-1000™, or ORTHOMATRIX™ HA-500™ hydroxyapatite particulate preparations. The hydroxyapatite or tricalcium phosphate may also be prepared by known methods, such as those disclosed by Termine, et al., *Arch Biochem Biophys* (1970) 140:307-325, or by Hayashi, K. et al., *Arch Orthop Trauma Surg* (supra). In any event, the mineral is generally and preferably of non-biological origin and is supplied as a powder of appropriate mesh. Preferred particle sizes are in the range of 100–2000μ. While the mineral content of bone could be harvested and purified for this purpose, more economically prepared and controlled compositions are preferable, both as a matter of cost and of quality. If solid blocks are desired, these are prepared from the particulate form as described below.

The collagen component of the composition is critical to its efficiency. Numerous forms of collagen have been prepared and they differ in their physical properties as well as in their biocompatibility. It does not appear, however, that the particle size is relevant within the range of diameters over which a mixture will be a solution, colloid, or suspension, and in order to permit use of a single generic term, "collagen dispersion" is used herein to refer to a collagen preparation in aqueous medium in which the collagen particle size is not specified—i.e., the preparation may be a solution, suspension, or gel.

Native collagen consists mainly of a triple helical structure containing repeating triplet sequences composed of glycine linked to two additional amino acids, commonly proline and hydroxyproline. Native collagen contains regions at each end which do not have the triplet glycine sequence, and thus do not form helices. These regions are thought to be responsible for the immunogenicity associated with most collagen preparations, and the immunogenicity can be mitigated by the removal of these regions to produce "atelopeptide" collagen. This can be accomplished by digestion with proteolytic enzymes, such as trypsin and pepsin. The non-helical telopeptide regions are also responsible for natively occurring cross-linking, and atelopeptide collagen must be cross-linked artificially if cross-linking is desired.

Naturally occurring collagens have been subclassified into about ten types, depending on the amino acid sequence in the individual chains, the carbohydrate content, and the presence or absence of disulfide cross-links. The most common subtypes are Type I, which is present in skin, tendon, and bone, and which is made by fibroblasts; and Type III, which is found primarily in skin. Other types reside in specialized membranes or cartilage, or at cell surfaces. Types I and III contain similar numbers of amino acids in their helices and have a high degree of homology; however, Type III, but not Type I, contains two adjacent cysteines at the C-terminal ends of the triple helix, which are capable of forming inter-chain cross-links.

Therefore, collagen preparations may differ from each other by virtue of their initial compositions which is a function of their origin, or by virtue of their modes of preparation. Collagen derived from bone, for example, contains exclusively Type I collagen; while collagen derived from skin also contains Type III. Also, the process of preparation may or may not remove the telopeptides. Thus both unaltered and "atelopeptide" collagen are possible. Cross-linking may be effected deliberately or accidentally. Sterilization by γ-irradiation or by high heat may result in cross-linking without control of extent or nature and results in partial degradation of the triple helix; deliberate cross-linking may be carried out by a variety of means, including treatment with glutaraldehyde. Differences arising from perhaps more subtle causes are perhaps the result of variations in the details of the preparation procedure. For example, the collagen may be solubilized and re-precipitated, or may simply be finely divided and kept in suspension. When the solubilized material is reaggregated, the aggregation may be done in ways so as to form non-specifically bonded solids, or the collagen may be reconstituted into fibers which simulate the native form. Also, of course, the degree of purity may vary.

As used herein, "free from impurities" or "purified" as regards collagen preparations refers to those impurities which are normally associated with collagen in its native state. Thus, collagen prepared from calfskin is free from impurities when other components of calfskin have been removed; that from bone when other components of bone are eliminated.

"Reconstituted" collagen refers to collagen which has been disassembled into individual triple helical molecules, with or without their telopeptide extensions, brought into solution and then regrouped into "fibrillar" forms. In this form, the fibrils consist of long, thin collagen molecules staggered relative to one another by multiples of about one-fourth their length. Thus results in a banded structure which can be further aggregated into fibers.

Collagen which is "substantially free from cross-linking" refers to collagen which has had the atelopeptides removed, and thus lacks the native capacity for cross-link formation. These preparations remain substantially cross-link free if not deliberately cross-linked by, for example, being treated with glutaraldehyde or subjected to treatment imposing a spurious form of linkage—for example, treatments often used for sterilizing purpose, such as high temperature and γ-radiation.

The collagen suitable for use in the invention is a purified atelopeptide fibrillar reconstituted collagen.

One suitable collagen preparation which meets these specifications is an atelopeptide collagen which is reconstituted into fibrillar form and supplied as a dispersion of 5–100 mg/ml preferably around 50–70 mg/ml. Such dispersions as ZYDERM® Collagen Implant (ZCI), which is commercially available in preparations containing 35 mg/ml collagen or 65 mg/ml collagen in saline, manufactured by Collagen Corporation, Palo Alto, Calif., are appropriate. For use in the compositions of the inventions, the ZCI or other collagen dispersions are used without lidocaine or other sedative drugs. As used herein, "ZCI" refers to the aqueous collagen dispersion, rather than to the collagen component per se.

The compositions of the invention contain 50–85% by weight of calcium phosphate mineral component, preferably 65–75% mineral component, and the balance is a collagen dispersion such as ZCI. In terms of the mineral/collagen ratio (excluding the aqueous dispersion component), the mixtures are 60–98% mineral, preferably 75–98% mineral and the rest collagen. The composition may be prepared simply by mixing the two components into a cohesive mass and then loading the mixture into an appropriate container which is packaged directly to supply a "wet" product. Alternatively, the mixture is cast into a desired shape (e.g., blocks, squares sheets) and then lyophilized or air dried and packaged to provide a "dry" product. The degree of dryness obtained is, of course, arbitrary, since both "wet" and "dry" forms are usable. However, as used herein, the "dry" form refers to mixtures containing <1.0% moisture. For lyophilized material, substantially all moisture is removed. The dry material is rigid and can be cut with a sharp instrument.

If cross-linking is desired, glutaraldehyde to a level of 0.001–0.1% is used to treat the dry product after drying, or high temperature treatment is applied to the dry product. For cross-linking the wet product, glutaraldehyde may also be used and the excess then removed by washing.

Additional components may be added to the composition of the invention if desired, including bone marrow, blood, and saline. The percentages given above refer to the composition of the collagen/mineral mixture only; this combination mixture forms from 10–100% by weight of the composition supplied to the subject.

The resulting composition is used to augment bone and fill bony defects, for example, periodontal bony pockets, tooth extraction sockets, and jaw cysts. An important example of onlay procedures includes alveolar ridge augmentation. The procedures for the surgical implantation are known in the art. For alveolar ridge augmentation, the composition is inserted under the periosteum in places where augmentation is desired. In orthopedic and reconstructive applications, mineral in the form of porous blocks may also be indicated, particularly where the graft must bear stress. Implantation of the collagen-impregnated blocks is effected by standard surgical techniques.

An alternative composition comprises a porous but rigid mineral block shaped as desired for the application and coated with collagen from a collagen dispersion that has been infiltrated into the pores porous blocks of hydroxyapatite and/or tricalcium phosphate are known and available. Blocks are made from the powdered form by compacting in the presence of liquid and then drying.

A typical procedure for preparing a powder or block impregnated with collagen is shown in FIG. 1. A mold of the desired shape is fabricated of a suitable material such as stainless steel. The mold is made up of a body and two removable, screened ends (the end plate and fill head). Each end has a tubuation in order to attach a tubing through which the collagen gel will flow. The screens are of a sufficiently small size to retain HA particles, yet permit the flow of the collagen gel.

The end piece is attached to the mold, and the mold filled with HA as a powder or a block to the desired volume. The remaining end piece (the filling head) is lowered to the upper level of HA to seal the mold. The collagen dispersion, preferably a gel, is pumped into the mold until flow is detected from the outflow; the mold and HA may be evacuated to assist injection and minimize air entrapment. The conglomerate may optionally be compressed before removing the head plates and ejecting the implant.

The collagen gel content of composites prepared following the foregoing method are limited to the void space between the HA particles. For example, the use of 20–40 mesh HA will yield a ratio of 25:75 collagen to HA by weight. The resulting material is more rigid with increased HA content.

The foregoing method is, of course, not limited to preparations of the invention, but can be used to provide collagen coated pores in calcium phosphate mineral blocks for a wide range of collagen preparations.

The solid block forms of the mixtures of the invention, whether prepared by compaction of the mineral followed by collagen coating or by drying a collagen/mineral mixture, may be cured to obtain greater integrity-under stress by various curing treatments.

In one process, a heat-curing process, the air-dried composite, in block form, which must contain less than 1% moisture before treatment, is heated to 60°–120° C., preferably 75°–90° C., for 4–168 hours, preferably 6–72 hours. The curing may take place either in open or closed containers. The resulting blocks are considerably more rigid and resistant to pressure than the uncured materials.

In an alternate curing process, longer times, but lower temperatures, are employed. In one such process, the composite, while still wet, is cured in a moistened state in a closed container for 1–10 days at 37° C. and then dried at ambient temperature −37° C. to dryness. This material is relatively rigid, but can be further cured using the heat-curing process above.

In still another curing method, the mixture is subjected to cross-linking while still in a wet state and then dried at ambient temperature −37° C. to dryness, optionally followed by heat curing. For the cross-linking, one usable procedure is to incubate the wet block at 37° C. for 1–10 days, preferably 1–2 days, in the presence of a vaporized cross-linking agent such as the vapors of glutaraldehyde. This process is most conveniently conducted in a closed container to confine the vapors. After suitable cross-linking, the composite is dried at ambient −37° C. until a moisture content of less than 1% is achieved.

In the alternative, cross-linking can be achieved by soaking the wet mixture in the cross-linking reagent solution. Such a solution contains, for example, 0.001–1%, preferably 0.001–0.005% glutaraldehyde or formaldehyde. Treatment lasts for 4–48 hours. preferably around 24 hours, and is conducted at ambient temperature. After washing with sterile water to remove excess cross linking agent, the composite is dried at ambient temperature −37° C. as above.

The results of the foregoing curing processes are, in general, superior values of the compressive modulus $\epsilon$ measured in N/cm$^2$ (N=Newtons).

CRANIAL ONLAY MODEL

The compositions of the invention were tested in a cranial onlay model. Rats, 8–10 weeks old, were anesthetized and the scalp reflected. A coronal incision was made in the periosteum, which was then elevated to form a tent sufficient to accommodate placement of a single implant directly on the bony surface of the cranium. Each rat received one implant of experimental or control material, and the periosteum was drawn over the implant and the scalp repositioned and sutured. The implant sites were evaluated by x-ray and histology at 4, 8, and 16 weeks post-implantation.

EXAMPLES

The following examples serve to illustrate but not to limit the invention.

EXAMPLE 1

ZCI/Hydroxyapatite

A mineral/collagen preparation was obtained by mixing 65 parts by weight of PERIOGRAF ® hydroxyapatite with 35 parts by weight of ZYDERM ® collagen implant (65 mg/ml) without lidocaine. (Since the ZCI is 6.5% collagen in saline, the final composition is 65 parts HA, 2.3 parts collagen (0.065×35) and 32.7 (35−2.3) parts saline, all by weight.)

To obtain the wet composition, the mixture was thoroughly mixed, and 0.4 ml portions placed into a widebore syringe for direct use. To obtain the dry preparation, portions measuring 0.55 ml were placed in a widebore syringe and the plunger removed to permit the mixture to dry. The mixture was dried under a Laminar Flow Hood (LFH), and the plunger replaced for convenient packaging.

Both the wet and dry compositions were used in the cranial onlay model. Thirty-six rats were used in the study: 12 were supplied implants of the dry mixture. 12 of the wet, and 12 hydroxyapatite alone as a control.

After 4 weeks, x-ray films showed that the air-dried implants held their shape and remained in a mound after placement. Wet implants or hydroxyapatite alone spread over the surface of the cranial vault. The hydroxyapatite particles averaged 3-4 layers in all types of implants.

Air-dried implants showed more extensive bone formation than wet implants, frequently extending from the base of the implant to the distal border, while osteogenic activity in wet implants was more uneven and generally limited to less than 50% of the thickness. Hydroxyapatite alone showed bone formation only around the first layer of particles adjacent to the skull. In all cases, bone formed in direct contact with the hydroxyapatite particles with no intervening tissue. Thus, fusion between new and preexisting bone occurred in all implants. However, bone marrow differentiation and the amount of bone was always greater in the air-dried implants according to histological studies. No inflammation was shown except for sequestering and encapsulation of hydroxyapatite particles not involved in layers contiguous to new bone formation.

Thus, the collagen composites increased the rate of bone fixation over hydroxyapatite alone. Air drying of composites also favors more extensive bone formation.

EXAMPLE 2

Effect of Curing

The mixtures as prepared in Example 1 (except that OrthoMatrix HA-1000 ® was used as the mineral component), wet or dry, as specified, were subjected to curing processes to ascertain the effect on rigidity. The dry material (less than 1% moisture) showed a compressive modulus ($\epsilon$) of 1.25 N/cm$^2$. This could be improved by subjecting the dry material to curing at elevated temperatures for various lengths of time. The results in Table 1 indicate that optimum results are achieved by heating at higher temperatures and longer times.

TABLE 1

| Temp. (°C.) | Time (hrs) | Compressive Modulus $\epsilon$ (N/cm$^2$) |
| --- | --- | --- |
| 60 | 72 | 3.35 |
| 60 | 96 | 3.87 |
| 60 | 120 | 4.0 |
| 60 | 144 | 4.1 |
| 80 | 24 | 5.7 |
| 80 | 48 | 6.3 |
| 80 | 72 | 6.3 |
| 80 | 96 | 7.0 |
| 80 | 120 | 7.6 |
| 80 | 144 | 10.5 |
| 80 | 168 | 11.0 |
| 100 | 4 | 4.1 |
| 100 | 16 | 6.1 |
| 100 | 26 | 6.75 |
| 100 | 48 | 7.55 |
| 120 | 10 | 14.3 |
| 120 | 26 | 16.7 |

An improved compressive modulus could also be achieved using a cross-linking process in solution conducted at 20° C. for 24 hours. The improvement was dependent on the cross-linking agent concentration; results for various concentrations of glutaraldehyde under these conditions are shown in Table 2.

TABLE 2

| Glutaraldehyde Conc. (%) | Compressive Modulus ($\epsilon$) |
| --- | --- |
| 0.001 | 13.9 |
| 0.002 | 16.15 |
| 0.003 | 18.0 |
| 0.004 | 21.0 |
| 0.005 | 24.15 |
| 0.01 | 32.0 |

Even simple incubation at 37° C. before drying was able to increase the compressive modulus considerably. A sample of the mixture in Example 1 was incubated at 37° C. for 168 hours before drying at ambient temperature to a moisture content of <1.0%. This composite exhibited a compressive modulus of 6.15 N/cm$^2$, as compared to the 1.25 N/cm$^2$ shown by the mixture dried immediately after mixing.

We claim:

1. A composition for use in bone repair, which composition comprises a mixture consisting essentially of 60–98% by weight of a calcium phosphate mineral component obtained from mineral particles of non-biological origin in admixture with 2–40% of an atelopeptide reconstituted fibrillar collagen.

2. The composition of claim 1 wherein the mineral component is selected from the group consisting of hydroxyapatite, tricalcium phosphate, and mixtures thereof, and
wherein the particles are 100–2000 μm.

3. The composition of claim 1 wherein the collagen is supplied as an aqueous suspension of 35 mg/ml–65 mg/ml.

4. The composition of claim 1 which contains less than 1% by weight water.

5. A method of repairing bone which comprises placing in contact with a fresh bone surface the composition of claim 1.

6. A process for preparing a composition for use in bone repair, which process comprises subjecting a dried mixture consisting essentially of 60–98% by weight of a calcium phosphate mineral component in admixture with 2–40% of an atelopeptide reconstituted fibrillar collagen component, said mixture containing less than 1% by weight water, to a temperature of 60°–120° C. for 4–168 hours.

7. The process of claim 6 wherein the mixture is treated at 75°–90° C. for 6–72 hours.

8. A composition which is the product of the process of claim 6.

9. A process for preparing a composition for use in bone repair, which composition comprises a mixture consisting of essentially 60–98% by weight of calcium phosphate mineral component in admixture with 2–40% of an atelopeptide reconstituted fibrillar collagen, which process comprises incubating said mixture in the presence of water at approximately 37° C. for 1–10 days, followed by drying said mixture to a moisture content of less than 1% by weight.

10. A composition which is the product of the process of claim 9.

11. The process of claim 9 which further includes subjecting the dried mixture to a temperature of 60°–120° C. for 4–168 hours.

12. A composition which is the product of the process of claim 11.

13. A process for preparing a composition for use in bone repair, which composition comprises a mixture consisting essentially of 60–90% by weight of calcium phosphate mineral component in admixture with 2–40% of an atelopeptide reconstituted fibrillar collagen, which process comprises exposing said mixture in the presence of water to the vapors of a cross-linking agent for a time and at a temperature effective to effect cross-linking of the collagen component, followed by drying said mixture to a moisture content of less than 1% by weight.

14. The process of claim 13 wherein the mixture is exposed to cross-linking agent at 37° C. for 1–10 days.

15. The process of claim 14 wherein the cross-linking agent is glutaraldehyde.

16. A composition for bone repair prepared by the process of claim 13.

17. The process of claim 13 which further includes subjecting the dried mixture to a temperature of 60°–120° C. for 4–168 hours.

18. A composition for bone repair prepared by the process of claim 17.

19. A process for preparing a composition for use in bone repair, which composition comprises a mixture consisting essentially of 60–98% by weight of a calcium phosphate mineral component in admixture with 2–40% of an atelopeptide reconstituted fibrillar collagen, which process comprises soaking said mixture in a solution containing cross-linking agent removing said cross-linking agent, and drying the mixture to a moisture content of less than 1% by weight.

20. The process of claim 19 wherein the cross-linking agent is selected from glutaraldehyde and formaldehyde at a concentration of 0.001–1.0%.

21. A composition for bone repair prepared by the process of claim 19.

22. The process of claim 19 which further includes subjecting the dried mixture to a temperature of 60°–120° C. for 4–168 hours.

23. A composition for bone repair prepared by the process of claim 22.

24. A process for preparing a composition for use in bone repair, which composition comprises a mixture consisting essentially of 60–98% by weight of a calcium phosphate mineral component in admixture with of an atelopeptide reconstituted fibrillar collagen, which process comprises drying the mixture to a moisture content of less than 1% by weight, then soaking said mixture in a solution containing cross-linking agent, removing said cross-linking agent, and redrying the mixture to a moisture content of less than 1%.

25. A composition for bone repair prepared by the process of claim 24.

26. A process for augmentation of bone defects which comprises applying to said defect the composition of claim 1.

27. The process of claim 26 wherein the bone defect is periodontal.

* * * * *